US006809077B2

(12) United States Patent
Or et al.

(10) Patent No.: US 6,809,077 B2
(45) Date of Patent: Oct. 26, 2004

(54) CYCLOSPORIN ANALOGS FOR THE TREATMENT OF AUTOIMMUNE DISEASES

(75) Inventors: Yat Sun Or, Cambridge, MA (US); Tsvetelina Ivanova Lazarova, Brookline, MA (US); Blake Christopher Hamann, Cambridge, MA (US); Jason Shih-Hao Chen, Claremont, CA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 9 days.

(21) Appl. No.: 09/976,219

(22) Filed: Oct. 12, 2001

(65) Prior Publication Data

US 2003/0104992 A1 Jun. 5, 2003

(51) Int. Cl.$^7$ .......................... A61K 38/13; A61K 38/12
(52) U.S. Cl. ................... 514/11; 514/2; 514/9; 514/828; 530/317; 530/318; 530/402; 424/278.1
(58) Field of Search .................. 514/11, 2, 9, 828; 530/317, 318, 402; 424/278.1; 604/19

(56) References Cited

U.S. PATENT DOCUMENTS

| 4,554,351 A | 11/1985 | Wenger ........................ 544/177 |
| 4,798,823 A | 1/1989 | Witzel ........................ 514/11 |
| 5,239,057 A | 8/1993 | Wang ........................ 530/321 |
| 5,427,960 A | 6/1995 | Wang ........................ 436/536 |
| 5,525,590 A | 6/1996 | Bollinger et al. ............ 514/11 |
| 5,643,870 A | 7/1997 | Boelsterli .................... 514/11 |
| 5,827,706 A | * 10/1998 | Leitner et al. ............... 435/536 |
| 6,605,593 B1 | 8/2003 | Naicker et al. ............... 514/11 |
| 2002/0132763 A1 | 9/2002 | Naicker et al. ............... 514/11 |

FOREIGN PATENT DOCUMENTS

| DE | 0296122 | * 12/1988 | ........... C07K/7/64 |
| EP | 0296122 A2 | 12/1988 | |
| EP | 0296122 B1 | 9/1993 | |
| WO | WO 99/18120 | 4/1999 | ........... C07K/7/64 |

OTHER PUBLICATIONS

Reference 1 (REF 1) (2003) "substitution reactions of benzene and other aromatic compound" p. 1, (http://www.cem.msu.edu/~reusch/VirtualText/benzrx1.htm).*
Billich, A. et al. (1987) Enzymatic synthesis of cyclosporin A. J. Biol. Chem. vol. 262., pp. 17258–17259.*
A Semi–Synthetic Approach To Olefinic Analogs Of Amino Acid One (MeBMT) In Cyclosporin A. Park, et al. Tetrahedron Letters, vol. 30, No. 32, pp 4215–4218, 1989.
Billich et al., Enzymatic Snythesis of CsA, J. Biol. Chem., 262, 17258–17259 (1987).
Faulds et al., Cyclosporin: A Review of its Pharmacodynamic and Pharmacokinetic Properties, and Therapeutic Use in Immunoregulatory Disorders, Drugs 46, 953–1040 (1993).

* cited by examiner

Primary Examiner—Karen Cochrane Carlson
Assistant Examiner—Samuel Wei Liu
(74) Attorney, Agent, or Firm—Jason D. Ferrone

(57) ABSTRACT

The present invention relates to a cyclosporin analog of the following formula (I) or a pro-drug or pharmaceutically acceptable salt thereof:

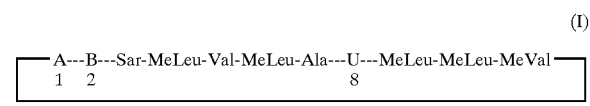

In particular, residue A maybe represented by either formula A1 or A2 as illustrated below:

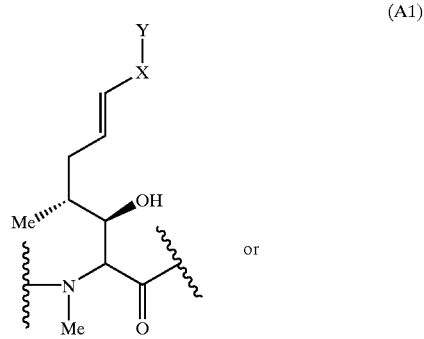

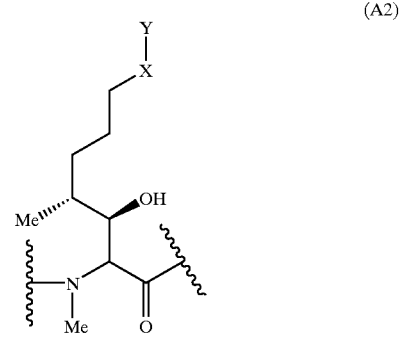

where X and Y are defined herein. In a second embodiment, the present invention relates to pharmaceutical compositions comprising pro-drugs or pharmaceutically acceptable salts of the compounds of the present invention and the use thereof for treating autoimmune diseases or for the prevention of organ transplantation rejection in a subject. In a third embodiment, the present invention relates to processes for the production of novel cyclosporin analogs of the present invention.

9 Claims, No Drawings

CYCLOSPORIN ANALOGS FOR THE TREATMENT OF AUTOIMMUNE DISEASES

TECHNICAL FIELD

The present invention relates to novel cyclosporin analogs and methods of treatment for the prevention of organ transplantation rejection and the treatment of autoimmune diseases in a subject. The present invention further relates to pharmaceutical compositions comprising the compounds of the present invention and processes for their production.

BACKGROUND OF THE INVENTION

The cyclosporins comprise a class of structurally distinctive, cyclic, poly-N-methylated undecapeptides, commonly possessing pharmacological activity, in particular immunosuppressive, anti-inflammatory or anti-parasitic activity. The first of the cyclosporins to be isolated was the naturally occurring fungal metabolite cyclosporin, Cyclosporin A represented as follows:

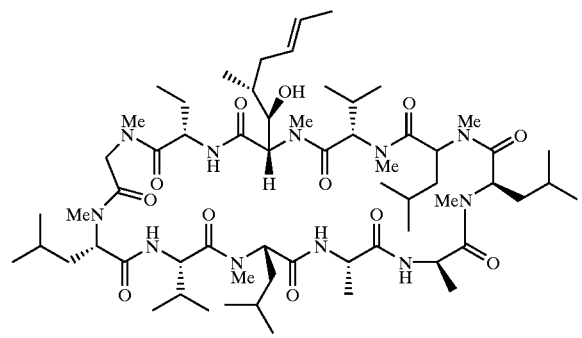

Since the original discovery of cyclosporin, a wide variety of naturally occurring cyclosporins have been isolated and identified, and many further non-natural cyclosporins have been prepared by total- or semi-synthetic means or by the application of modified culture techniques. The class comprising cyclosporins is thus now substantial and includes, for example, the naturally occurring Cyclosporins A through Z, for example, [Thr]$^2$, [Val]$^2$, [Nva]$^2$ and [Nva]$^{2-}$, [Nva]$^5$-Cyclosporin (also known as Cyclosporins C, D, G and M respectively), [(D)MeVal]$^{11}$-Cyclosporin (also known as Cyclosporin H), [cf., Traber et al.;1, Helv. Chim. Acta, 60, 1247–1255 (1977); Traber et al.; 2, Helv. Chim. Acta, 65, 1655–1667 (1982); Kobel et al.; Europ. J. Applied Microbiology and Biotechnology, 14, 273–240 1982); and Von Wartburg et al.; Progress in Allergy, 38, 28–45, 1986)]; as well as various non-natural cyclosporin derivatives and artificial or synthetic cyclosporin derivatives and artificial or synthetic cyclosporins including dihydrocyclosporins [in which the MeBmt-residue is saturated by hydrogenation]; derivatized cyclosporins (e.g., in which the 3'-O-atom of the MeBmt-residue is acylated or a further substituent is introduced at the α-carbon atom of the sarcosyl residue at the 3-position); and cyclosporins in which variant amino acids are incorporated at specific positions within the peptide sequence, for example, [3-O-acetyl-MeBmt]$^1$-Cyclosporin (also known as Dihydro-cyclosporin D), [(D)Ser]$^8$-Cyclosporin, [MeIle]$^{11}$-Cyclosporin, [MeAla]$^6$-Cyclosporin, [(D) Pro]$^3$-Cyclosporin etc., employing the total synthetic method for the production of cyclosporins developed by R. Wenger—see e.g. Traber et al., 1; Traber et al., 2; and Kobel et al., loc cit. U.S. Pat. Nos. 4,108,985, 4,220,641, 4,288,431, 4,554,351, 4,396,542 and 4,798,823; European Patent Publication Nos. 34,567A, 56,782A, 300, 784A and 300,785; International Patent Publication No. WO 86/02080 and UK Patent Publication Nos. 2,206,119 and 2,207,678; Wenger 1, Transpl. Proc., 15 Suppl. 1:2230 (1983); Wenger 2, Angew. Chem. Int. Ed. 24 77 (1985) and Wenger 3, Progress in the Chemistry of Organic Natural Products, 50, 123 (1986).

The compound Cyclosporin A has found wide use since its introduction in the fields of organ transplantation and immunomodulation, and has brought about a significant increase in the success rate for transplantation procedures. Undesired side effects associated with cyclosporin, such as nephrotoxicity, have led to a continued search for immunosuppressant compounds having improved, efficacy and safety.

SUMMARY OF THE INVENTION

The present invention relates to novel cyclosporin analogs and methods of treatment for the prevention of organ transplantation rejection and the treatment of autoimmune diseases in a subject. The present invention further relates to pharmaceutical compositions comprising the compounds of the present invention and processes for their production.

More particularly, the present invention relates to a cyclosporin analog of the following formula (I) or a pro-drug or pharmaceutically acceptable salt thereof:

(I)

In particular, residue A may be represented by either formula A1 or A2 as illustrated below:

(A1)

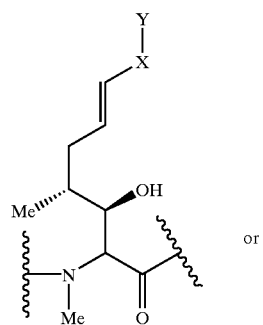

or

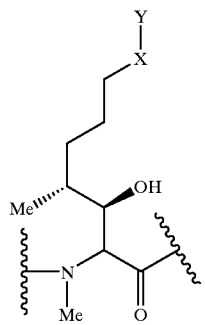

(A2)

where X is absent, —C1–C6-alkyl- or —C3–C6-cycloalkyl-; Y is selected from the groups: aryl, substituted aryl, heteroaryl, and substituted heteroaryl; residue B is -αAbu-, -Val-, -Thr- or -Nva-; and residue U is -(D)Ala-, -(D)Ser-, —[O-(2-hydroxyethyl)(D)Ser]-, —[O-acyl(D)Ser]- or —[O-(2-acryloxyethyl)(D)Ser]-.

In a second embodiment, the present invention relates to the use of the cyclosporin analogs of the present invention or a pro-drug or pharmaceutically acceptable salt thereof in pharmaceutical compositions for the treatment of autoimmune diseases or for the prevention of organ transplantation rejection in a subject.

In a third embodiment, the present invention relates to processes for the production of novel cyclosporin analogs of the present invention. In a preferred embodiment, the present invention relates to the processes for the production of cyclosporin analogs of formula I, where residue A may be represented by either formula A1 or A2.

The present invention also contemplates method(s) of treatment of autoimmune diseases or prevention of organ transplant rejection in a subject by administering to the subject therapeutically effective amounts of the cyclosporin analogs of the present invention with or without the concurrent use of other drugs or pharmaceutically acceptable carriers or excipients.

DETAILED DESCRIPTION OF THE INVENTION

The present invention relates to novel cyclosporin analogs and methods of treatment for the prevention of organ transplantation rejection and the treatment of autoimmune diseases in a subject. The present invention further relates to pharmaceutical compositions comprising the compounds of the present invention and processes for their production. The patents and publications identified in this specification indicate the knowledge in this field and are hereby incorporated by reference in their entirety. In the case of inconsistencies, the present disclosure will prevail.

More particularly, the present invention relates to a cyclosporin analog of the following formula (I) or a pro-drug or pharmaceutically acceptable salt thereof:

(I)

In particular, residue A maybe represented by either formula A1 or A2 as illustrated below:

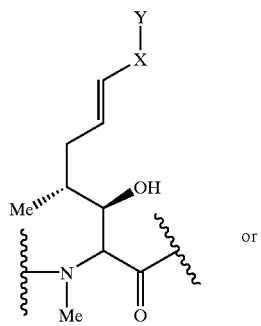

(A1)

or

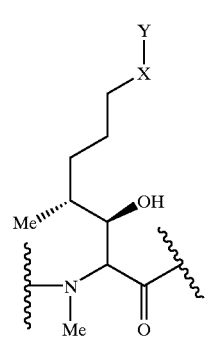

(A2)

where X is absent, —C1–C6-alkyl- or —C3–C6-cycloalkyl-; Y is selected from the groups: aryl, substituted aryl, heteroaryl, and substituted heteroaryl; residue B is -αAbu-, -Val-, -Thr- or -Nva-; and residue U is -(D)Ala-, -(D)Ser-, —[O-(2-hydroxyethyl)(D)Ser]-, —[O-acyl(D)Ser]- or —[O-(2-acryloxyethyl)(D)Ser]-.

In formula (I), abbreviation of amino acid residues, for example, -Ala-, MeLeu-, -αAbu-, etc., are in accordance with conventional practice and are to be understood as having the L-configuration unless otherwise indicated (for example, (D)Ala- represents a residue having the D-configuration). Abbreviation of residues preceded by "Me-" represents a α-N-methylated amino acid residue, for example, "Me-Leu" is a α-N-methylated-Leucine residue. Individual residues of the cyclosporin molecule are numbered, as in the art, clockwise and starting with the residue -MeBmt-, corresponding to residue 1. The same numerical sequence is employed throughout the present specification and claims.

In a most preferred embodiment, a cyclosporin analog of the present invention is represented by formula I or a pro-drug or pharmaceutically acceptable salt thereof, where residue B is -αAbu- and residue U is -(D)Ala-. In another preferred embodiment, a cyclosporin analog of the present invention is represented by formula I or a pro-drug or pharmaceutically acceptable salt thereof, where X is absent in residue A, residue B is -αAbu- and residue U is -(D)Ala-.

Representative compounds of the invention include, but are not limited to, the following compounds as illustrated below:

Compound of formula (I), where A=A1, X is absent and Y=Ph; B is -αAbu-; and U is -(D)Ala-.

Compound of formula (I), where A=A1, X is absent and Y=(2'-Me)Ph; B is -αAbu-; and U is -(D)Ala-.

Compound of formula (I), where A=A1, X is absent and Y=(4'-F)Ph; B is -αAbu-; and U is -(D)Ala-.

Compound of formula (I), where A=A1, X is absent and Y=(4'-CF3)Ph; B is -αAbu-; and U is -(D)Ala-.
Compound of formula (I), where A=A1, X is absent and Y=(2'-Br)Ph; B is -αAbu-; and U is -(D)Ala-.
Compound of formula (I), where A=A1, X is absent and Y=(2'-Cl)Ph; B is -αAbu-; and U is -(D)Ala-.
Compound of formula (I), where A=A1, X is absent and Y=(2'-OMe)Ph; B is -αAbu-; and U is -(D)Ala-.
Compound of formula (I), where A=A1, X is absent and Y=(3'-Cl)Ph; B is -αAbu-; and U is -(D)Ala-.
Compound of formula (I), where A=A1, X is absent and Y=(4'-Cl)Ph; B is -αAbu-; and U is -(D)Ala-.
Compound of formula (I), where A=A1, X is absent and Y=(3'-Br)Ph; B is -αAbu-; and U is -(D)Ala-.
Compound of formula (I), where A=A1, X is absent and Y=(4'-Br)Ph; B is -αAbu-; and U is -(D)Ala-.
Compound of formula (I), where A=A1, X is absent and Y=(3'-COOCH$_3$)Ph; B is -αAbu-; and U is -(D)Ala-.
Compound of formula (I), where A=A1, X is absent and Y=(4'-COOCH$_3$)Ph; B is -αAbu-; and U is -(D)Ala-.
Compound of formula (I), where A=A1, X is absent and Y=(2'- Naphthalene); B is -αAbu-; and U is -(D)Ala-.
Compound of formula (I), where A=A1, X is absent and Y=(4'-t-butyl)Ph; B is -αAbu-; and U is -(D)Ala-.
Compound of formula (I), where A=A1, X is absent and Y=(pentafluoro)Ph; B is -αAbu-; and U is -(D)Ala-.
Compound of formula (I), where A=A1, X is absent and Y=(4'-AcO—)Ph; B is -αAbu-; and U is -(D)Ala-.
Compound of formula (I), where A=A1, X is absent and Y=(4'-OCH$_3$)Ph; B is -αAbu-; and U is -(D)Ala-.
Compound of formula (I), where A=A1, X is absent and Y=(3', 4'-OMe$_2$)Ph; B is -αAbu-; and U is -(D)Ala-.
Compound of formula (I), where A=A1, X is absent and Y=(2',5'-Me$_2$)Ph; B is -αAbu-; and U is -(D)Ala-.
Compound of formula (I), where A=A1, X is absent and Y=Pyridine; B is -αAbu; and U is -(D)Ala-.
Compound of formula (I), where A=A1, X is absent and Y=Pyrrole; B is -αAbu; and U is -(D)Ala-.
Compound of formula (I), where A=A1, X is absent and Y=(N-methyl) Pyrrole; B is -αAbu; and U is -(D)Ala-.
Compound of formula (I), where A=A1, X is absent and Y=Thiophene; B is -αAbu; and U is -(D)Ala-.
Compound of formula (I), where A=A1, X is absent and Y=Oxazole; B is -αAbu; and U is -(D)Ala-.
Compound of formula (I), where A=A2, X is absent and Y=Ph; B is -αAbu-; and U is -(D)Ala-.
Compound of formula (I), where A=A2, X is absent and Y=(2'-Me)Ph; B is -αAbu-; and U is -(D)Ala-.
Compound of formula (I), where A=A1, X is absent and Y=(S)Ph; B is -αAbu-; and U is -(D)Ala-.
Compound of formula (I), where A=A1, X is absent and Y=(SO)Ph; B is -αAbu; and U is -(D)Ala-.
Compound of formula (I), where A=A1, X is absent and Y=(SO$_2$)Ph; B is -αAbu; and U is -(D)Ala-.

The potent immunomodulatory activity which compounds of the instant invention demonstrate in common in vitro biological assays (for example, calcineurine assay, nuclear factor of activated T cells (NFAT) reporter gene assay, murine and human mixed lymphocyte reaction) or animal models (for example delayed-type hypersensitivity response—DTH, popliteal lymph node assay—PLN) indicate that these compounds possess immunosuppressive, antimicrobial, antifungal, antiviral, antiinflammatory, and antiproliferative activity, and possess the ability to reverse chemotherapeutic drug resistance. As agents block T-cell activation, a prerequisite for human immunodeficiency virus (HIV) proliferation, the compounds are useful as prophylactics for the prevention of HIV replication. The compounds of the invention would be useful when used alone, or in combination therapy with other immunosuppressants, for example, but not limited to, FK506, rapamycin, cyclosporin A, picibanil, mycophenolic acid, azathioprine, prednisolone, cyclophosphamide, brequinar and leflunomide.

As immunosuppressants, the compounds of the present invention are useful when administered for the prevention of immune-mediated tissue or organ graft rejection. Examples of transplanted tissues and organs which suffer from these effects are heart, kidney, liver, medulla ossium, skin, cornea, lung, pancreas, intestinum tenue, limb, muscle, nervus, duodenum, small-bowel, pancreatic-islet-cell, and the like; as well as graft-versus-host diseases brought about by medulla ossium transplantation. The regulation of the immune response by the compounds of the invention would also find utility in the treatment of autoimmune diseases, such as rheumatoid arthritis, systemic lupus erythematosis, hyperimmunoglobulin E, Hashimoto's thyroiditis, multiple sclerosis, progressive systemic sclerosis, myasthenia gravis, type I diabetes, uveitis, allergic encephalomyelitis, glomerulonephritis, and the like; and further infectious diseases caused by pathogenic microorganisms, such as HIV. In the particular cases of HIV-1, HIV-2 and related retroviral strains, inhibition of T-cell mitosis would suppress the replication of the virus, since the virus relies upon the host T-cell's proliferative functions to replicate.

Further uses include the treatment and prophylaxis of inflammatory and hyperproliferative skin diseases and cutaneous manifestations of immunologically-mediated illnesses, such as psoriasis, atopical dermatitis, contact dermatitis and further eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne and Alopecia areata; various eye diseases (autoimmune and otherwise) such as keratoconjunctivitis, vernal conjunctivitis, keratitis, herpetic keratitis, conical cornea, dystrophia epithelialis corneae, corneal leukoma, ocular pemphigus, Mooren's ulcer, Scieritis, Graves' opthalmopathy, Vogt-Koyanagi-Harada syndrome, sarcoidosis, multiple myeloma, etc.; obstructive airway diseases, which includes conditions such as chronic obstructive pulmonary disease (COPD) asthma (for example, bronchial asthma, allergic asthma, intrinsic asthma, extrinsic asthma and dust asthma), particularly chronic or inveterate asthma (for example, late asthma and airway hyper-responsiveness), bronchitis, allergic rhinitis and the like; inflammation of mucosa and blood vessels such as gastric ulcers, vascular damage caused by ischemic diseases and thrombosis. Moreover, hyperproliferative vascular diseases such as intimal smooth muscle cell hyperplasia, restenosis and vascular occlusion, particularly following biologically- or mechanically-mediated vascular injury can be treated or prevented by the compounds of the invention.

Other treatable conditions would include but are not limited to schemic bowel diseases, inflammatory bowel diseases, necrotizing enterocolitis, intestinal lesions associated with thermal burns and leu kotriene B$_4$-mediated diseases; intestinal inflammations/allergies such as Coeliac diseases, proctitis, eosinophilic gastroenteritis, mastocytosis, Crohn's disease and ulcerative colitis; food-related allergic diseases which have symptomatic manifestation remote from the gastro-intestinal tract (e.g., migraine, rhinitis and eczema); renal diseases such as interstitial nephritis, Goodpasture's syndrome, hemolytic-uremic syndrome and diabetic nephropathy; nervous diseases such as multiple myositis, Guillain-Barre syndrome, Menieres disease, polyneuritis, multiple neuritis, mononeuritis and radiculopathy; endocrine diseases such as hyperthyroidism and Basedow's disease; hematic diseases such as pure red cell aplasia, aplastic anemia, hypoplastic anemia, idiopathic thrombocytopenic purpura, autoimmune hemolytic anemia, agranu locytosis, pernicious anemia, megaloblastic anemia and anerythroplasia; bone diseases such as osteoporosis; respiratory diseases such as sarcoidosis, fibroid lung and idiopathic interstitial pneumonia; skin disease such as dermatomyositis, leukoderma vulgaris, ichthyosis vulgaris, photoallergic sensitivity and cutaneous T cell lymphoma; circulatory diseases such as arteriosclerosis, atherosclerosis, aortitis syndrome, polyarteritis nodosa and myocardosis; collagen diseases such as scleroderma, Wegener's granuloma and Siogren's syndrome; adiposis; eosinophilic fasciitis; periodontal disease such as lesions of gingiva, periodontium, alveolar bone and substantia ossea dentis; nephrotic syndrome such as glomerulonephritis; male pattern aleopecia or alopecia senilis by preventing epilation or providing hair germination and/or promoting hair generation and hair growth; muscular dystrophy; Pyoderma and Sezary's syndrome; Addison's disease; active oxygen-mediated diseases, as for example organ injury such as ischemia-reperfusion injury of organs (such as heart, liver, kidney and digestive tract) which occurs upon preservation, transplantation or ischemic disease (for example, thrombosis and cardiac infraction): intestinal diseases such as endotoxin-shock, pseudomembranous colitis and colitis caused by drug or radiation; renal diseases such as ischemic acute renal insufficiency and chronic renal insufficiency; pulmonary diseases such as toxinosis caused by lung-oxygen or drug (for example, paracort and bleomycins), lung cancer and pulmonary emphysema; ocular diseases such as cataracta, siderosis, retinitis, pigmentosa, senile macular degeneration, vitreal scarring and corneal alkali burn; dermatitis such as erythema multiforme, linear IgA ballous dermatitis and cement dermatitis; and others such as gingivitis, periodontitis, sepsis, pancreatitis, diseases caused by environmental pollution (for example, air pollution), aging, carcinogenis, metastasis of carcinoma and hypobaropathy; disease caused by histamine or leukotnene-$C_4$ release; Behcet's disease such as intestinal-, vasculo- or neuro-Behcet's disease, and also Behcet's which affects the oral cavity, skin, eye, vulva, articulation, epididymis, lung, kidney and so on. Furthermore, the compounds of the invention are useful for the treatment and prevention of hepatic disease such as immunogenic diseases (for example, chronic autoimmune liver diseases such as the group consisting of autoimmune hepatitis, primary biliary cirrhosis and sclerosing cholangitis), partial liver resection, acute liver necrosis (e.g., necrosis caused by toxin, viral hepatitis, shock or anoxia), B-virus hepatitis, non-A/non-B hepatitis, cirrhosis (such as alcoholic cirrhosis) and hepatic failure such as fulminant hepatic failure, late-onset hepatic failure and "acute-on-chronic" liver failure (acute liver failure on chronic liver diseases), and moreover are useful for various diseases because of their useful activity such as augmention of chemotherapeutic effect, preventing or treating activity of cytomegalovirus infection, particularly human cytomegalovirus (HCMV) infection, anti-inflammatory activity, and so on.

The compounds of the present invention may be used as vaccines to treat immunosuppression in a subject. It is sometimes found that the antigen introduced into the body for the acquisition of immunity from disease also acts as an immunosuppressive agent, and therefore, antibodies are not produced by the body and immunity is not acquired. By introducing a compound of the present invention into the body as a vaccine, the undesired immunosuppression may be overcome and immunity acquired.

The compounds of the present invention may also find utility in the chemosensitization of drug resistant target cells. Cyclosporin A and FK-506 are known to be effective modulators of P-glycoprotein, a substance which binds to and inhibits the action of anticancer drugs by inhibiting P-glycoprotein, as they are capable of increasing the sensitivity of multidrug resistant (MDR) cells to chemotherapeutic agents. It is believed that the compounds of the invention may likewise be effective at overcoming resistance expressed to clinically useful antitumour drugs such as 5-fluorouracil, cisplatin, methotrexate, vincristine, vinblastine and adriamycin, colchicine and vincristine.

Further, it has recently been shown that the steroid receptor-associated heat shock proteins (hsn or HSP), hsp56 or hsp59, belong to the class of immunophilin proteins (see "HSP70 induction by cyclosporin A in cultured rat hepatocytes: effect of vitamin E succinate," And res, David et al., *Iristituto de Bioqimica, Facuftad de Farmacia, Universidad Complutense, Madrid, Spain.* J. Hepatol. (2000) 33(4), 570–579; "Cyclosporin A Induces an Atypical Heat Shock Response," Paslaru, Liliana, et al., Unite de Genetique Moleculaire, Paris, Fr. Biochem. Biophys. Res. Commun. (2000), 269(2), 464–469;"The cyclosporine A-binding immunophilin CyP-40 and the FK506-binding immunophilin hsp56 bind to a common site on hsp90 and exist in independent cytosolic heterocomplexes with the untransformed glucocorticoid receptor," Owens-Grillo, Janet K. et al., Med. Sch., Univ. Michigan, Ann Arbor, Mich. USA. J. Biol. Chem. (1995), 270(35), 20479–84). The ability of a steroid receptor-associated heat shock protein to bind the immunosuppressive CsA suggests that the steroid receptor and immunophilin signal transduction pathways are functionally interrelated. The combined treatment of compounds of the present invention and low concentrations of a steroid ligand (for e.g., progesterone, dexamethasone) result in a significant enhancement of target gene expression over that seen in response to ligand alone. Thus, the compounds of the present invention potentiate steroid-mediated transactivation.

Aqueous liquid compositions of the present invention may be particularly useful for the treatment and prevention of various diseases of the eye such as autoimmune diseases (including, for example, conical cornea, keratitis, dysophia epithelialis corneae, leukoma, Mooren's ulcer, sclevitis and Graves' ophthalmopathy) and rejection of corneal transplantation.

Accordingly, the pharmaceutical compositions of the present invention comprise a therapeutically effective amount of a cyclosporin analog of the invention in combination with a pharmaceutically acceptable carrier or excipient. In particular, compositions pertaining to the present invention are useful for treating a subject for immune-mediated organ or tissue allograft rejection, a graft-versus-host disease, an autoimmune disease, a reversible obstructive airway disease, a hyperproliferative disease, or an ischemic or inflammatory intestinal or bowel disease.

The present invention also relates to method(s) of treatment of autoimmune diseases or prevention of organ transplant rejection in a subject by administering to the subject therapeutically effective amounts of the cyclosporin analogs of the present invention with or without the concurrent use of other drugs or pharmaceutically acceptable excipients, as described throughout the present specification.

The methods of the present invention comprise treating a subject in need of immunosuppressive, anti-inflammatory, antimicrobial, antifungal, antiviral or antiproliferative therapy, or requiring the reversal of chemotherapeutic drug resistance, by administering a therapeutically effective amount of a compound of the invention for such time and in such amounts as is necessary to produce the desired result.

As used in the present invention, "therapeutically effective amount" of one of the compounds means a sufficient amount of the compound to treat a particular disease, at a reasonable benefit/risk ratio. The compounds of the present invention may be employed in pure form or, where such forms exist, in pharmaceutically acceptable salt, ester or prodrug forms. Alternatively, the compound may be administered as pharmaceutical compositions containing the compound of interest in combination with one or more drugs or pharmaceutically acceptable excipients. It will be understood, however, that the total daily usage of the compounds and compositions of the present invention will be decided by the attending physician within the scope of sound medical judgment.

The specific therapeutically-effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.001 to about 10 mg/kg of patients body mass/day. For purposes of oral administration, more preferable doses may be in the range of from about 0.005 to about 3 mg/kg/day. If desired, the effective daily dose may be divided into multiple doses for purposes of administration; consequently, single dose compositions may contain such amounts or submultiples thereof to make up the daily dose.

Definitions

The terms "$C_1$–$C_3$-alkyl" or "$C_1$–$C_6$-alkyl" as used herein refer to saturated, straight- or branched-chain hydrocarbon radicals containing between one and three or one and six carbon atoms, respectively. Examples of $C_1$–$C_3$ alkyl radicals include methyl, ethyl, propyl and isopropyl, and examples of $C_1$–$C_6$-alkyl radicals include, but are not limited to, methyl, ethyl, propyl, isopropyl, n-butyl, tert-butyl, neopentyl and n-hexyl.

The term "$C_3$–$C_6$-cycloalkyl-" as used herein refers to carbocyclic groups of 3 to 6 carbons, respectively; for example, cyclopropyl, cyclobutyl, cyclopentyl and cyclohexyl.

The term "aryl" as used herein refers to a carbocyclic ring system having one or more aromatic rings including, but not limited to, phenyl, naphthyl, tetrahydronaphthyl, indanyl, indenyl and the like. Aryl groups (including multi-cyclic aryl groups) can be unsubstituted or substituted with one, two or three substituents independently selected from lower alkyl, substituted loweralkyl, haloalkyl, alkoxy, thioalkoxy, lower alkylenedioxy, lower alkylidenedioxy, amino, alkylamino, dialkylamino, acyamino, cyano, hydroxy, acyl, halo and/or trifluoromethyl, mercapto, nitro, carboxylaldehyde, carboxy, alkoxycarbonyl, carbamoyl, sulfamoyl, lower alkoxycarbonylamino, lower alkanoyl, ureido, amidino and carboxamide.

The term "substituted aryl" as used herein refers to an aryl group as defined herein substituted independently by replacement of one, two or three of the hydrogen atoms thereon with the groups specified above, including but not limited to, Cl, Br, F, I, OH, CN, $C_1$–$C_3$-alkyl, $C_3$–$C_6$-alkoxy, $C_1$–$C_6$-alkoxy, $C_3$–$C_6$-alkoxy substituted with aryl, haloalkyl, thioalkoxy, amino, alkylamino, mercapto, nitro, carboxylaldehyde, carboxy, alkoxycarbonyl and carboxamide. For example, but not limited to, substituted aryl groups include tetrafluorophenyl and pentafluorophenyl.

The term "heteroaryl" or "heterocyclics," as used herein, refers to a cyclic aromatic radical, optionally partially hydrogenated, having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isoxazolyl, carboxy-lower alkyl(oxo) oxazoyl, for example, 2,5-dihydro-3-oxo-1,2-oxazoyl, thiadiazolyl, 4,5-dihydrothiadiazolyl, oxadiazolyl, thiophenyl, furanyl, quinolinyl, isoquinolinyl, and the like.

The term "substituted heteroaryl" as used herein refers to a heteroaryl group as defined herein substituted by independently replacing one, two, or three of the hydrogen atoms thereon with groups specified above including, but not limited to, Cl, Br, F, I, OH, CN, $C_1$–$C_6$-alkyl, $C_1$–$C_6$-alkoxy, $C_1$–$C_6$-alkoxy substituted with aryl, haloalkyl, thioalkoxy, amino, alkylamino, dialkylamino, mercapto, nitro, carboxylaldehyde, carboxy, alkoxycarbonyl and carboxamide. In addition, any one substituent may be an aryl, heteroaryl, or heterocycloalkyl group.

The terms "halo" and "halogen" as used herein refer to an atom selected from fluorine, chlorine, bromine and iodine.

The term "subject" as used herein refers to a mammal or animal. Preferably the mammal is a human. A subject as used herein refers to, for example, dogs, cats, horses, cows, pigs, guinea pigs and the like.

The term "pro-drug" as used herein refers to pharmacologically acceptable derivatives, for example, but not limited to, esters and amides, such that the resulting biotransformation product of the derivative is the active drug. Pro-drugs are known in the art and are described generally in, e.g., Goodman and Gilman's "Biotransformation of Drugs," in the Pharmacological Basis of Therapeutics, $8^{th}$ Ed., McGraw Hill, Int. Ed. 1992, page 13–15, which is hereby incorporated by reference in its entirety.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in J. Pharmaceutical Sciences, 66: 1–19 (1977), which is incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counterions such as halide, hydroxide, carboxylate, sulfate, phosphate, nitrate, loweralkyl sulfonate and aryl sulfonate.

| Abbreviations | |
|---|---|
| Sar: | Sarcosine |
| MeLeu: | N-Methyl-Leucine |
| Val: | Valine |
| Ala: | Alanine |
| MeVal: | N-Methyl Valine |
| Et: | Ethyl |
| Ph: | Phenyl |
| Fmoc: | 9-Fluorenylmethoxycarbonyl- |
| MeBmt: | N-Methyl-(4R)-4-[(E)-2-butenyl]-4-methyl-L-threonine |
| α-Abu: | α-Aminobutyric acid |

Synthetic Methods

The compounds and processes of the present invention will be better understood, but are not limited to, the synthetic schemes, Schemes I and II, which illustrate the methods by which the compounds of the present invention (illustrated by formula I) may be prepared. The groups X and Y, and the amino acid residues B and U in formula I are as defined earlier in the specification. The starting material for Scheme I, illustrated by formula I where A=-MeBmt-, may be, for example, but not limited to, a fermentation product or a synthetic product made by solution phase chemistry. Preferably, the starting material is commercially available. The starting material as a fermentation product may be made from highly productive strains, for example, but not limited to, *Sesquicillopsis rosariensis* G. ARNOLD F605; *Tolypocladium inflatum* wb6-5; Fusant, *Tolypocladium inflatum* KD461 etc. (in U.S. Pat. Nos. 5,256,547; 5,856,141 etc.). Alternately, the starting material may be made by solution phase chemistry either by sequentially assembling amino acids or by linking suitable small peptide fragments, where the units are linked by, for example, but not limited to, amide, ester or hydroxylamine linkages (described in, Müller, *Methoden der organischen,* Chemie Vol. XV/2, pp 1 to 364, Thieme Verlag, Stuttgart, 1974; Stewart, Young, Solid Phase Peptide Synthesis, pp 31 to 34, 71 to 82, Pierce Chemical Company, Rockford, 1984; Bodanszky, Klausner, Ondetti, Peptide Synthesis, pp 85 to 128, John Wiley & Sons, New York, 1976 and other standard books on solution phase peptide chemistry). For amide linkages particular preference is given to the azide method, the symmetric and mixed anhydride method, in situ generated or preformed active esters and methods using coupling reagents (e.g., dicyclohexylcarbodiimide, N,N-dimethyl-4-aminopyridine, N-hydroxy-benzotriazole, PyBrop® etc.). Classical solution phase chemistry using standard Z- and Boc-methodology may be used.

Residue A, which is -MeBmt- in the starting material is further modified, as illustrated in the following reaction schemes.

Scheme I:

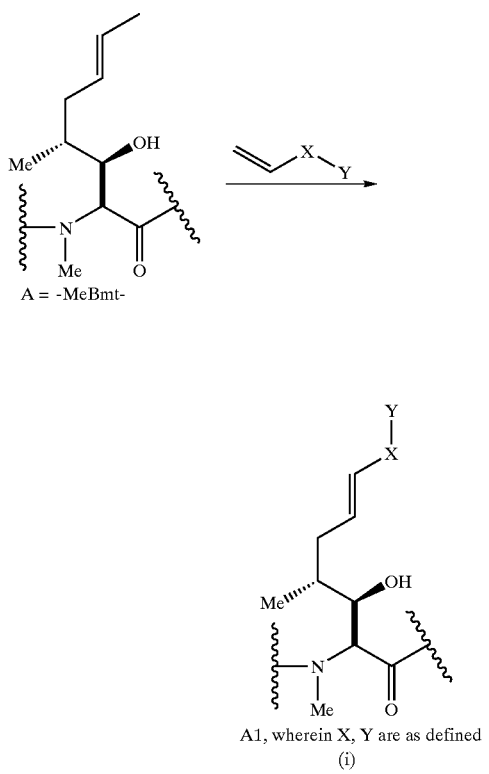

A1, wherein X, Y are as defined
(i)

Scheme II:

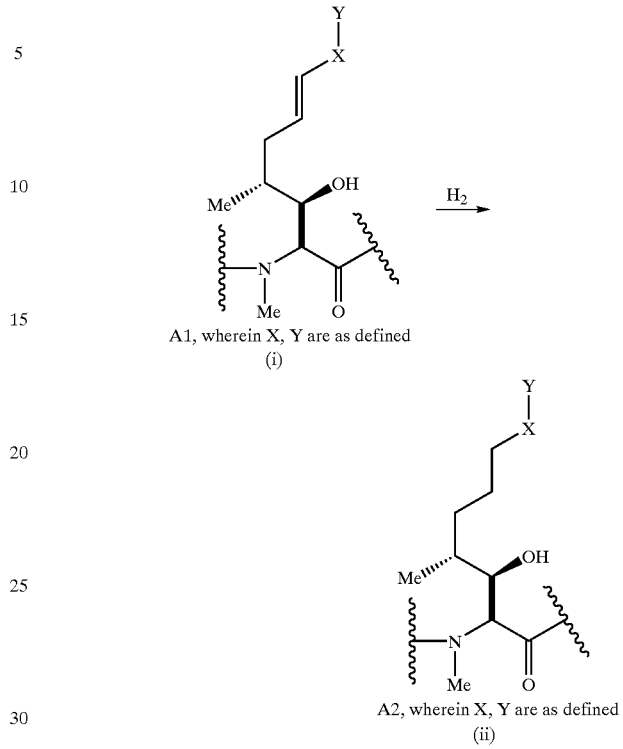

A2, wherein X, Y are as defined
(ii)

The process for the preparation of the compounds of formula I comprises reacting a compound of formula I, where A=-MeBmt- (for example, Cyclosporin A) with an olefin having a terminal double bond with catalysts such as Grubb's ruthenium alkylidene, Grubbs dihydroimidazole ruthenium, Shrock-Hoveyda molybdenum catalysts or benzylidene catalysts [see (a) U.S. Pat. No. 6,111,121; (b) Reviews: Synlett, 1999, 2, 267; (c) Reviews: Ivin, K J; Mol, J. C. *Olefin Metathesis and Metathesis Polymerization*, $2^{nd}$ ed., Academic Press, New York, 1997; (d) *J. Org. Chem.*, 1999, 64, 4798–4816; (e) *Angew. Chem.*, Int. Ed. English, 1997, 36, 2036–2056; (f) *Tetrahedron* 1998, 54, 4413–4450.] or Nolan's ruthenium catalyst [see (a) International Patent Application No. WO 00/15339; (b) *Org. Lett.*, 2000, 2, 1517–1519; (c) *J. Org. Chem.*, 2000, 65, 2204–2207] or Molybdenum catalysts [see (a) *J. Am. Chem. Soc.*, 1990, 112, 3875 (b), *J. Am. Chem. Soc.*, 1996, 118, 10926–10927] in the presence of a lithium salt such as lithium bromide, lithium chloride, lithium trifluoroacetate, lithium triflate of a lewis acid such as titanium isopropoxide in an organic solvent. The organic solvent used may be solvents such as, for example, dichloromethane, chloroform, toluene, benzene, tetrahydrofuran, dimethylformamide and the like or mixtures thereof. The reaction may be carried out from room temperature to about 100° C. for 1–7 days to provide a compound of formula I, where residue A is converted to residue A1 having formula (i).

The compounds of formula I in an organic solvent, where residue A1 is of formula (i), are then subjected to standard hydrogenation conditions using a catalyst such as, but not limited to, catalytic amounts of palladium on carbon in a hydrogen atmosphere to provide the saturated compounds of formula I, where in particular, residue A1 having formula (i) is converted to residue A2 having formula (ii).

The organic solvents used can be solvents such as methanol, ethanol, ethyl acetate or mixtures thereof. Other catalysts useful to assist hydrogenation may be, for example, but not limited to, platinum metal or its oxide [see standard books on catalytic hydrogenation, e.g., Rylander, P. N., *Hydrogenation Methods*, Academic Press: NY, 1985; *Catalytic Hydrogenation in Organic Synthesis*, Academic Press: NY, 1985; Cerveny, L., *Catalytic Hydrogenation*, Elsevier: NY, 1986 etc.]. The reaction may be carried out at room temperature or elevated temperature, for example, but not limited to, 50° C. or 100° C.

Pharmaceutical Compositions

In the pharmaceutical compositions of the present invention, a compound of the invention is combined with a pharmaceutically acceptable excipient, meaning a non-toxic solid, semi-solid or liquid filler, diluent, encapsulating material or formulation auxiliary of any type. The compositions may be administered orally, rectally, parenterally, intracisternally, intravaginally, intraperitoneally, topically (as by powders, ointments, drops or transdermal patch), bucally, or as an oral or nasal spray. The term "parenteral" as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically-acceptable sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity may be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption, such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues.

The injectable formulations may be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically-acceptable excipient or carrier, such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules may be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions may contain, in addition to the active compounds, suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes, for example, but not limited to, administration to the skin or mucosa, including surfaces of the lung and eye. If necessary topical administration may be combined with other modes of administration, such as but not limited to, a combined topical and systemic mode of administration. Compositions for topical administration, including those for inhalation, may be prepared as a dry powder which may be pressurized or non-pressurized. In non-pressurized powder compositions, the active ingredient in finely divided form may be used in admixture with a larger-sized pharmaceutically-acceptable inert carrier comprising particles having a size, for example, of up to 100 micrometers in diameter. Suitable inert carriers include sugars such as lactose. Desirably, at least 95% by weight of the particles of the active ingredient have an effective particle size in the range of 0.01 to 10 micrometers.

Alternatively, the composition may be pressurized and contain a compressed gas, such as nitrogen or a liquefied gas propellant. The liquefied propellant medium and indeed the total composition is preferably such that the active ingredient does not dissolve therein to any substantial extent. The pressurized composition may also contain a surface active agent, such as a liquid or solid non-ionic surface active agent or may be a solid anionic surface active agent. It is preferred to use the solid anionic surface active agent in the form of a sodium salt.

A further form of topical administration is to the eye, as for the treatment of immune-mediated conditions of the eye such as autoimmune diseases, allergic or inflammatory conditions, and corneal transplants. The compound of the invention is delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/cilary, lens, choroid/retina and sclera. The pharmaceutically acceptable ophthalmic vehicle may, for example, be an ointment, vegetable oil or an encapsulating material.

Compositions for rectal or vaginal administration are preferably suppositories which may be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., *Methods in Cell Biology*, Volume XIV, Academic Press, New York, N.Y. (1976), p. 33 et seq.

EXAMPLES

The procedures described above for preparing the compounds of the present invention will be better understood in connection with the following examples, which are intended to be illustrative only and not limiting of the scope of the invention. Various changes and modifications of the disclosed embodiments will be apparent to those skilled in the art. Such changes and modifications, including without limitation, those relating to the chemical structures, substituents, derivatives, intermediates, syntheses, formulations, assay protocols and/or methods of the invention may be made without departing from the spirit of the invention and the scope of the appended claims.

Example 1

Compound of Formula (I), where A=A1, X is Absent and Y=Ph; B is -αAbu-; and U is -(D)Ala- Styrene (0.1 ml, 0.83 mmol) and 1,3-bis(2,4,6-trimethylphenyl)imidazol-2-ylinene (tricyclohexylphosphine)dichloro ruthenium(II) bexylidene (Nolan catalyst, 0.0072 g, 0.0083 mmol) were added to a solution of Cyclosporin A (0.1 g, 0.083 mmol) in methylene chloride (3 ml) at room temperature. The reaction mixture was heated at 40° C. After 36 hours, more Nolan catalyst (0.0072 g, 0.0083 mmol) and styrene (0.048 ml, 0.45 mmol and the reaction was heated at 40° C. for additional 48 hours. After being cooled to room temperature, the reaction mixture was purified by column chromatography using one Biotage 40S columns (wash with hexane, dichloromethane, elution with 40/1 dichloromethane/methanol). Removal of solvent in vacuo gave the title compound as an off-white solid (0.118 g). Electrospray mass spectrum (ESMS) M+H: 1264.86

Example 2

Compound of Formula (I), where A=A1, X is Absent and Y=(2'-Me)Ph; B is -αAbu-; and U is -(D)Alao-Methyl styrene (0.248 g, 2.1 mmol) and 1,3-bis(2,4,6-trimethylphenyl)imidazol-2-ylinene (tricyclohexylphosphine)dichloro ruthenium(II) bexylidene (Nolan catalyst, 0.0361 g, 0.041 mmol) were added to a solution of Cyclosporin A (0.5 g, 0.416 mmol) in methylene chloride (3 ml) at room temperature. The reaction mixture was heated at 40° C. After 36 hours, more Nolan catalyst (0.0361 g, 0.041 mmol) and o-methyl styrene (0.248 g, 2.1 mmol and the reaction was heated at 40° C. for additional 48 hours. After being cooled to room temperature, the reaction mixture was purified by column chromatography using 2 Biotage 40S columns (wash with ether, 3% methanol in ether, 5% methanol in ether, elution with 10% methanol in ether). Removal of solvent in vaccuo gave the title compound as an off-white solid (0.243 g, 46% yield). Electrospray mass spectrum (ESMS) M+H: 1278.82

Example 3

Compound of Formula (I), where A=A1, X is Absent and Y=(4'-F)Ph; B is -αAbu-; and U is -(D)Ala- The title compound of Example 3 was prepared from Cyclosporin A, 4-fluoro styrene and Nolan catalyst according to the procedures described in Example 1. ESMS M+H: 1282.85

Example 4

Compound of Formula (I), where A=A1, X is Absent and Y=(4'-CF3)Ph; B is -αAbu-; and U is -(D)Ala- The title compound of Example 4 was prepared from Cyclosporin A, 4-trifluoro styrene and Nolan catalyst according to the procedures described in Example 1. ESMS M+H: 1332.84

Example 5

Compound of Formula (I), where A=A1, X is Absent and Y=(2'-Br)Ph; B is -αAbu-; and U is -(D)Ala- The title compound of Example 5 was prepared from Cyclosporin A, 2-bromo styrene and Nolan catalyst according to the procedures described in Example 1. ESMS M+H: 1342.77

Example 6

Compound of Formula (I), where A=A1, X is Absent and Y=(2'-Cl)Ph; B is -αAbu-; and U is -(D)Ala- The title compound of Example 6 was prepared from Cyclosporin A, 2-chloro styrene and Nolan catalyst according to the procedures described in Example 1. ESMS M+H: 1298.82

Example 7

Compound of Formula (I), where A=A1, X is Absent and Y=(2'-OMe)Ph; B is -αAbu-; and U is -(D)Ala- The title compound of Example 7 was prepared from Cyclosporin A, 2-methoxy styrene and Nolan catalyst according to the procedures described in Example 1. ESMS M+H: 1294.87

Example 8

Compound of Formula (I), where A=A1, X is Absent and Y=(3'-Cl)Ph; B is -αAbu-; and U is -(D)Ala- The title compound of Example 8 was prepared from Cyclosporin A, 3-chloro styrene and Nolan catalyst according to the procedures described in Example 1. ESMS M+H: 1298.83

Example 9

Compound of Formula (I), where A=A1, X is Absent and Y=(4'-Cl)Ph; B is -(αAbu-; and U is -(D)Ala- The title compound of Example 9 was prepared from Cyclosporin A, 4-chloro styrene and Nolan catalyst according to the procedures described in Example 1. ESMS M+H: 1298.83

Example 10

Compound of Formula (I), where A=A1, X is Absent and Y=(3'-Br)Ph; B is -αAbu-; and U is -(D)Ala- The title compound of Example 10 was prepared from Cyclosporin A, 3-bromo styrene and Nolan catalyst according to the procedures described in Example 1. ESMS M+H: 1342.78

Example 11

Compound of Formula (I), where A=A1, X is Absent and Y=(4'-Br)Ph; B is -αAbu-; and U is -(D)Ala- The title compound of Example 11 was prepared from Cyclosporin A, 4-bromo styrene and Nolan catalyst according to the procedures described in Example 1. ESMS M+H: 1342.78

Example 12

Compound of Formula (I), where A=A1, X is Absent and Y=(3'-COOCH$_3$)Ph; B is -αAbu-; and U is -(D)Ala- The title compound of Example 12 was prepared from Cyclosporin A, 3-vinylbenzoic acid methyl ester and Nolan catalyst according to the procedures described in Example 1. ESMS M+H: 1322.87.

Example 13

Compound of Formula (I), where A=A1, X is Absent and Y=(4'-COOCH$_3$)Ph; B is -αAbu-; and U is -(D)Ala- The title compound of Example 13 was prepared from Cyclosporin A, 4-vinylbenzoic acid methyl ester and Nolan catalyst according to the procedures described in Example 1. ESMS M+H: 1322.87.

Example 14

Compound of Formula (I), where A=A1, X is Absent and Y=(2'-Naphthalene); B is -αAbu-; and U is-(D)Ala- The title compound of Example 14 was prepared from Cyclosporin A, 2-vinylnaphthalene and Nolan catalyst according to the procedures described in Example 1. ESMS M+H: 1314.88.

Example 15

Compound of Formula (I), where A=A1, X is Absent and Y=(4'-t-butyl)Ph; B is -αAbu-; and U is -(D)Ala- The title compound of Example 15 was prepared from Cyclosporin A, 4-t-butyl styrene and Nolan catalyst according to the procedures described in Example 1. ESMS M+H: 1320.93.

Example 16

Compound of Formula (I), where A=A1, X is Absent and Y=(pentafluoro)Ph; B is -αAbu-; and U is -(D)Ala- The title compound of Example 16 was prepared from Cyclosporin A, pentafluoro styrene and Nolan catalyst according to the procedures described in Example 1. ESMS M+H: 1354.82.

Example 17

Compound of Formula (I), where A=A1, X is Absent and Y=(4'-AcO—)Ph; B is -αAbu-; and U is -(D)Ala- The title compound of Example 17 was prepared from Cyclosporin A, 4-acetoxy styrene and Nolan catalyst according to the procedures described in Example 1. ESMS M+H: 1322.87.

Example 18

Compound of Formula (I), where A=A1, X is Absent and Y=(4'-OCH$_3$)Ph; B is -αAbu-; and U is -(D)Ala- The title compound of Example 18 was prepared from Cyclosporin A, 4-methoxy styrene and Nolan catalyst according to the procedures described in Example 1. ESMS M+H: 1294.88.

Example 19

Compound of Formula (I), where A=A1, X is Absent and Y=(3', 4'-OMe$_2$)Ph; B is -αAbu-; and U is -(D)Ala- The title compound of Example 19 was prepared from Cyclosporin A, 3,4-dimethoxy styrene and Nolan catalyst according to the procedures described in Example 1. ESMS M+H: 1324.89.

Example 20

Compound of Formula (I), where A=A1, X is Absent and Y=(2',5'-Me$_2$)Ph; B is -αAbu-; and U is -(D)Ala- The title compound of Example 20 was prepared from Cyclosporin A, 2,5-dimethyl styrene and Nolan catalyst according to the procedures described in Example 1. ESMS M+H: 1292.90.

Example 21

Compound of Formula (I), where A=A2, X is Absent and Y=Ph; B is -αAbu-; and U is -(D)Ala- The title compound of Example 1 (0.050 g, 0.039 mmol) and palladium on carbon (0.0021 g, 0.002 mmol) were added to a flask and the flask was evacuated and backfilled with hydrogen gas three times. Anhydrous methanol (3 ml) was added and the reaction was stirred for 18 h at ambient temperature under an atmosphere of hydrogen. Afterwards the compound was purified by filtration through a pre-packed silica cartridge (3 g silica gel, elution with 3% methanol in ether). Concentration in vaccuo afforded the product as a white solid (0.018 g, 36% yield). Electrospray mass spectrum (ESMS) M+Na 1303.06

Example 22

Compound of Formula (I), where A=A2, X is Absent and Y=(2'-Me)Ph; B is -αAbu-; and U is -(D)Ala- The title compound of Example 21 is prepared from the title compound of Example 2 and hydrogen in the presence of palladium on carbon.

Example 23

Compound of Formula (I), where A=A1, X is Absent and Y=Pyridine; B is -αAbu; and U is -(D)Ala- The title compound of Example 23 is prepared from Cyclosporin A, 2-vinyl pyridine and Nolan catalyst according to the procedures described in Example 1.

Example 24

Compound of Formula (I), where A=A1, X is Absent and Y=Pyrrole; B is -αAbu; and U is -(D)Ala- The title compound of Example 24 is prepared from Cyclosporin A, 2-vinyl pyrrole and Nolan catalyst according to the procedures described in Example 1.

Example 25

Compound of Formula (I), where A=A1, X is Absent and Y=(N-methyl) Pyrrole; B is -αAbu; and U is -(D)Ala- The title compound of Example 25 is prepared from Cyclosporin A, 2-vinyl N-methyl pyrrole and Nolan catalyst according to the procedures described in Example 1.

Example 26

Compound of Formula (I), where A=A1, X is Absent and Y=Thiophene; B is -αAbu; and U is -(D)Ala- The title compound of Example 26 is prepared from Cyclosporin A, 2-vinyl thiophene and Nolan catalyst according to the procedures described in Example 1.

Example 27

Compound of Formula (I), where A=A1, X is Absent and Y=Oxazole; B is -αAbu; and U is -(D)Ala- The title compound of Example 27 is prepared from Cyclosporin A, 2-vinyl oxazole and Nolan catalyst according to the procedures described in Example 1.

The cyclosporins of the present invention have potent immunosuppressive anti-inflammatory activity. In particular they inhibit antigen-induced inflammatory cell infiltration, for example, into the airways. In vivo this activity is apparent following topical administration, e.g., via the pulmonary route.

Anti-inflammatory and immunosuppressive properties of the cyclosporins of the invention may be demonstrated in standard test models in vitro and in vivo, examples are as follows.

Example 28

Calcineurine Inhibition Assay

The immunosuppressive activity of cyclosporin is mediated through inhibition of the phosphatase activity of the enzyme calcineurin by a cyclophilin-cyclosporin complex. Thus, calcineurin inhibition is widely used as an in vitro measure of the activity of cyclosporin analogs.

Compounds were tested in an assay based on the Biomol Green Calcineurine Assay Kit supplied by Biomol (Plymouth Meeting, Pa.), supplemented with Cyclophilin A for enzyme inhibition. The activity of the recombinant human calcineurin was determined by release of phosphate from a phosphopeptide representing a fragment of camp-dependent protein kinase. Phosphate release was determined using the colorimetric detection reagent Biomol Green (Biomol AK-111).

Compounds in dimethyl sulfoxide (DMSO) (2.4 µl) were added to a 96-well microplate and mixed with 50 µl assay buffer (50mM Tris-HCl, pH 7.5; 100mM sodium chloride; 6 mM magnesium chloride; 0.5 mM dithiothreitol, 0.025% NP-40, 500 µM calcium chloride, 0.27 µM Calmodulin) containing 10 µM Cyclophilin and 3 nM Calcineurin. After warming to 37° C. for 60 mins, the enzymatic reaction was initiated by addition of phosphopeptide (7.5 μl) to give a final concentration of 94 μM. Phosphate release after 60 min at 37° C. was determined by addition of Biomol Green (100 μl) and measurement of the absorbance at 620 nm after 15 mins at room temperature.

$IC_{50}$ values were calculated from determinations of enzyme activity at inhibitor concentrations ranging from about 0.1 to about 0.0015 μM. Some representative $IC_{50}$ values of the compounds of the present invention, determined using the calcineurin assay are illustrated below:

| EP number | $IC_{50}$ (μM) |
|---|---|
| EP-000309 | 1.001 |
| EP-000863 | 0.512 |
| EP-000865 | 0.234 |
| EP-001320 | 0.061 |
| EP-001401 | 0.324 |
| EP-001402 | 0.378 |
| EP-001403 | 0.261 |
| EP-001404 | 0.352 |
| EP-001417 | 0.321 |
| EP-001418 | 0.763 |
| EP-001419 | 0.508 |
| EP-001424 | 0.649 |
| EP-001480 | 0.504 |
| EP-001481 | 0.379 |
| EP-001498 | 0.694 |
| EP-001552 | 0.281 |
| EP-001554 | 2.617 |

Example 29

NFAT Reporter Gene Assay

NFAT activation follows precisely the activation of calcineurin by increased free calcium levels in the cytoplasm. Researchers from diverse fields are interested in the NFAT family of transcription factors, which are potential targets for newer and safer immunosuppressive drugs. In addition, the activation of NFAT proteins involves various cellular signal transduction pathways, including calcium mobilization and mitogen-activated protein kinase (MAP kinase) pathways linked to T-cell receptors and Ras1. To assist researchers probing the activity of NFAT proteins, Stratagene has developed a PathDetect cis-reporter plasmid, the pNFAT-Luc reporter plasmid (Stratagene, Inc. catalog #219094), containing the NFAT binding site from the human IL-2 gene.2,7–9. The NEAT cis-reporting system includes the transfection-ready pNFAT-Luc reporter plasmid and the pCIS-CK negative control plasmid.

Construction of the pNFAT-Luc Plasmid:

The backbone of the 5749-base-pair pNFAT-Luc plasmid is the pFR-Luc reporter plasmid of the aforementioned PathDetect trans-reporting system. To this backbone, the GAL4 binding element was replaced with four direct repeats of the NFAT binding sequence (−286 to −257) from the IL-2 gene promoter, the most studied and widely used NFAT binding sequence. For all reporter plasmids of the PathDetect cis-reporting systems, activation of the luciferase gene indicated interaction of uncharacterized gene products, extracellular stimuli, growth factors, or drug candidates with specific enhancer elements. Then a plasmid expressing the gene of interest was cotransfected into mammalian cells along with a cis-reporter plasmid to indicate transcription activation.

Testing the pNFAT-Luc Plasmid in Jurkat Cells:

Pharmacology studies have established that NFAT proteins can be activated by the protein kinase C activator phorbol ester (PMA) in combination with the calcium ionophore ionomycin, reagents that raise free intracellular calcium. When Jurkat cells, a mature human T-cell line, or Chinese hamster ovary cells (CHO cells) were transfected with the pNFAT-Luc plasmid and treated with 60 ng/ml of PMA and 1 μg/ml of inomycin, luciferase activity increased by 13- and 16-fold, respectively. Therefore, the enhancer element in the pNFAT-Luc plasmid is responsive to calcium mobilization. Cells transfected with pNFAT-Luc and then treated with either PMA or onomycin alone did not show a significant increase in luciferase activity.

Cyclosporin inhibits the activity of calcineurin, a protein phosphatase regulated by intracellular calcium mobilization. All the isoforms of NFAT protein contain a calcineurin-binding domain and are activated by calcineurin. The inhibition of luciferase expression from pNFAT-Luc in the present model, in both Jurkat and CHO cells induced by PMA and ionomycin, was monitored for cyclosporin (as a positive control) and the cyclosporin analogs of the present invention.

In another set of experiments, rat basophilic leukemia cells stably transfected with chemokine receptors were transfected with pNFAT-Luc and then treated with their respective ligands (data not shown). When both luciferase expression and calcium levels were monitored in these cells, luciferase expression correlated very well with calcium mobilization. Therefore, luciferase expression from pNFAT-Luc indeed reflects the activation of endogenous NFAT proteins by calcium immobilization.

Example 30

Immunosuppressive Activity and Applications

Murine Mixed Lymphocyte Reaction

Ca. $0.5 \times 10^6$ lymphocytes from the spleen of female (8–10 weeks) Balb/c mice are incubated for 5 days in 0.2 ml cell growth medium with ca. $0.5 \times 10^6$ lymphocytes from the spleen of female (8–10 weeks) albino brown Agouti (CBA) mice. Test substance is added to the medium at various concentrations. Activity is assessed by ability to suppress proliferation-associated DNA synthesis as determined by incorporation of radiolabelled thymidine.

Mishell-Dutton Test

Ca. $10^7$ lymphocytes from the spleen of CF1, female mice are co-cultured with ca. $3 \times 10^7$ sheep erythrocytes for 3 days. Test substance is added to the incubation medium in varying concentrations. Lymphocytes are harvested and plated onto agar with fresh sheep erythrocytes as antigen. Sensitized lymphocytes secrete antibody that coats the erythrocytes, which lyse to form a plaque in the presence of complement. Activity is assessed by reduction in the number of plaque forming, i.e., antibody product, cells.

Delayed-Type Hypersensitivity Resonse

On Day 0 groups of ten mice (having BALB/cByJ or any other acceptable strain) are dosed with test compound (1 to 10%), vehicle or the positive control, cyclophosphamide (Cyclosporin A), and monitored from Day-2 to 7. The mice are anesthetized and their abdomens shaved. 100 μl of a 3% solution of ovalbumin are applied to the abdomen and dried. Seven days later, the mice are challenged by applying 5 μl of ovalbumin to each side of the right ear. After 24 hours, both the right and left ear thickness are measured using a micrometer caliper.

Popliteal Lymph Node Assay

First, an inducer (phenytoin) is injected into the mice footpad (having BALB/cByJ or any other acceptable strain). Then the mice are challenged (subcutaneously or po) with ester and control agent using graded doses, for example, 2.5, 10, 20 mg/Kg (based on Cyclosporin A data). On day 7 the popliteal lymph nodes are excised from the dosed mice and the lymph nodes are weighed. Then single cell suspensions of each lymph node are prepared and enumerated. The weight index for each animal is calculated (for example, a mean weight index <2 would indicate suppression of immune response).

Influence on Allergen-Induced Pulmonary Eosinophilia (in vitro)

Male Himalayan spotted guinea pigs (300 g, BRL) are sensitized to ovalbumin (OA) by i.p. injection of 1 ml of a suspension of OA (10 μg/ml) with $Al(OH)_3$ (100 mg) and B-pertussis vaccine (0.25 ml) in saline (0.9% w/v). For oral studies, the procedure is repeated 1× after 2 weeks and the animals are used one week later. For inhalation studies, the procedure is repeated 2× at 3-week intervals and the animals are used one week after the last injection.

Challenge is effected employing a saline solution of OA, nebulized for discharge into an exposure chamber. Test animals are exposed to OA by nose-only inhalation for 60 minutes. For inhalation studies, OA solution is used at a concentration of 0.01%.

Test substance is administered (a) inhalation and/or (b) orally. For oral studies, test substance is administered p.o. in olive oil 1× daily for 3 days or in powder form in methylcellulose once prior to OA challenge. On day 3, test animals receive test substance 1.5 hrs. prior to and 6 hrs. after OA challenge. For inhalation studies, test substance is micronised for delivery to test animals restrained within a flow-past, nose-only inhalation chamber. Administration by inhalation is effected 15 mins. prior to OA challenge.

Efficacy of administered test substance is determined by bronchoalveolar lavage (BAL) and cell counting. For this purpose animals are sacrificed with Na pento-barbitone (100 mg/kg i.p.) and the trachea is exposed and cannulated. 5 successive 10 ml aliqots of $Ca^{2+}$ and $Mg2+$ free Hank's balanced salt solution (HBSS), containing bovine serum albumin (BSA, 0.3%), EDTA (10 mM) and 4-(2-hydroxyethyl)-1-piperazineethanesulfonic acid (HEPES) (10 mM) is then introduced into the lung and immediately aspirated by gentle compression of the lung tissue. Total cell counts in pooled eluates are determined using an automatic cell counter. Lavage fluid is centrifuged at 200 g for 10 minutes and the cell pellet resuspended in 1 ml of supplemented HBSS. 10 μl of this cell suspension is added to 190 μl of Turk's solution (1:20 dilution). Differential cell counts are made from smears stained by Diff-Quick. Cells are identified and counted under oil immersion (×1,000). A minimum of 500 cells per smear are counted and the total population of each cell type is calculated.

In untreated animals, OA challenge induces increase of all cell types in BAL fluid 24 hours after challenge. Prior administration of cyclosporin analogs in accordance with the present invention at dosages of the order from about 1.0 to 15.0 mg/kg reduces eosinophil count in BAL in a dose dependent manner as compared with untreated controls. Cell counts for other leucocytes (macrophages, neutrophils etc.) are also reduced.

What is claimed is:

1. A cyclosporin analog of formula (I) or a pro-drug or a pharmaceutically acceptable salt thereof;

(I)

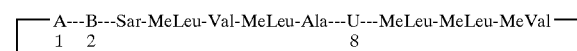

wherein
(i) A is of the formula:

(A1)

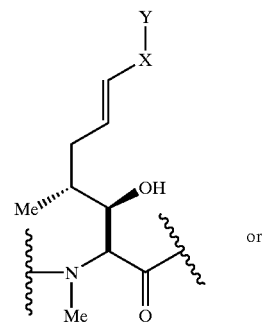

or (A2)

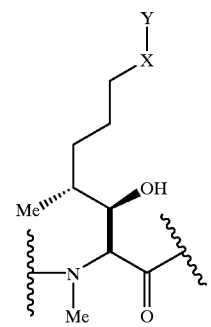

wherein:
X is absent, —$C_1$–$C_6$ alkyl-, or —$C_3$–$C_6$ cycloalkyl-;
Y is selected from the group consisting of:
(a) aryl substituted with one or more substituents independently selected from: —CN, $C_3$–$C_8$-alkoxy, $C_1$–$C_6$-alkoxy, $C_3$–$C_6$-alkoxy substituted with aryl, haloalkyl, thioalkoxy, amino, alkylamino, mercapto, nitro, carboxaldehyde, carboxy, alkoxycarbonyl, or carboxamide;
(b) heteroaryl; or
(c) substituted heteroaryl;
(ii) B is -αAbu-, -Val-, -Thr- or -Nva-; and
(iii) U is -(D)Ala-, -(D)Ser-, —[O-(2-hydroxyethyl)(D)Ser]-, —[O-(acyl)(D)Ser]- or —[O-(2-acyloxyethyl)(D)Ser]-.

2. A cyclosporin analog of claim 1 defined by formula (I), wherein X is absent and Y is phenyl substituted at the ortho position with a substituent independently selected from: —CN, $C_3$–$C_6$-alkoxy, $C_1$–$C_6$-alkoxy, $C_3$–$C_8$-alkoxy substituted with aryl, haloalkyl, thioalkoxy, amino, alkylamino, mercapto, nitro, carboxaldehyde, carboxy, alkoxycarbonyl, or carboxamide.

3. A cyclosporin analog according to claim 1 or a pro-drug or a pharmaceutically acceptable salt thereof, selected from the group consisting of:

Compound of formula (I), where A=A1, X is absent and Y=(4'-$CF_3$)Ph; B is -αAbu-; and U is -(D)Ala-;

Compound of formula (I), where A=A1, X is absent and Y=(2'-OMe)Ph; B is -αAbu-; and U is -(D)Ala-;

Compound of formula (I), where A=A1, X is absent and Y=(3'-$COOCH_3$)Ph; B is -αAbu-; and U is -(D)Ala-;

Compound of formula (I), where A=A1, X is absent and Y=(4'-$COOCH_3$)Ph; B is -αAbu-; and U is -(D)Ala-;

Compound of formula (I), where A=A1, X is absent and Y=(2=-Naphthalene); B is -αAbu-; and U is -(D)Ala-;

Compound of formula (I), where A=A1, X is absent and Y=(4'-t-butyl)Ph; B is -αAbu-; and U is -(D)Ala-;

Compound of formula (I), where A=A1, X is absent and Y=(4'-AcO-)Ph; B is -αAbu-: and U is -(D)Ala-;

Compound of formula (I), where A=A1, X is absent and Y=(4'-$OCH_3$)Ph; B is -αAbu-; and U is -(D)Ala-;

Compound of formula (I), where A=A1, X is absent and Y=(3', 4'-$OMe_2$)Ph; B is -αAbu-; and U is -(D)Ala-;

Compound of formula (I), where A=A1, X is absent and Y=Pyridine; B is -αAbu; and U is -(D)Ala-;

Compound of formula (I), where A=A1, X is absent and Y=Pyrrole; B is -αAbu; and U is -(D)Ala-;

Compound of formula (I), where A=A1, X is absent and Y=(N-methyl) Pyrrole; B is -αAbu; and U is -(D)Ala-;

Compound of formula (I), where A=A1, X is absent and Y=Thiophene; B is -αAbu; and U is -(D)Ala-;

Compound of formula (I), where A=A1, X is absent and Y=Oxazole; B is -αAbu; and U is -(D)Ala-;

Compound of formula (I), where A=A1, X is absent and Y=(S)Ph; B is -αAbu; and U is -(D)Ala-;

Compound of formula (I), where A=A1, X is absent and Y=(SO)Ph; B is -αAbu; and U is -(D)Ala-; and Compound of formula (I), where A=A1, X is absent and Y=($SO_2$)Ph; B is -αAbu; and U is -(D)Ala-.

4. A pharmaceutical composition, said composition comprising at least one cyclosporin analog of formula (I) as claimed in claim 1, said cyclosporin analog being present alone or in combination with a pharmaceutically acceptable carrier or excipient.

5. A compound according to claim 1, wherein X is absent and Y is substituted heteroaryl group.

6. A compound according to claim 1, wherein X is absent and Y is (2'-methyl)furan-2-yl group.

7. A method for treating autoimmune diseases in a subject, which comprises the step of administering to said subject a therapeutically effective amount of at least one cyclosporin analog of formula (I) as claimed in claim 1.

8. The method of claim 7, wherein said autoimmune disease is selected from conical cornea, keratitis, dysophia epithelialis cornea, leukoma, Mooren's ulcer, sclevitis and Grave's ophthalmopathy.

9. A method for preventing organ transplantation rejection in a subject, which comprises the step of administering to said subject a therapeutically effective amount of at least one cyclosporin analog of formula (I) as claimed in claim 1.

* * * * *